United States Patent
Datta et al.

(10) Patent No.: US 9,650,651 B2
(45) Date of Patent: May 16, 2017

(54) METHOD FOR PRODUCTION OF N-PROPANOL AND OTHER C3-CONTAINING PRODUCTS FROM SYNGAS BY SYMBIOTIC CO-CULTURES OF ANAEROBIC MICROORGANISMS

(71) Applicants: Rathin Datta, Chicago, IL (US); Michael Enzien, Lisle, IL (US); Robert Hickey, Okemos, MI (US); William Levinson, Naperville, IL (US)

(72) Inventors: Rathin Datta, Chicago, IL (US); Michael Enzien, Lisle, IL (US); Robert Hickey, Okemos, MI (US); William Levinson, Naperville, IL (US)

( * ) Notice: Subject to any disclaimer, the term of this patent is extended or adjusted under 35 U.S.C. 154(b) by 0 days.

(21) Appl. No.: 13/802,905

(22) Filed: Mar. 14, 2013

(65) Prior Publication Data
US 2014/0273120 A1    Sep. 18, 2014

(51) Int. Cl.
| | | |
|---|---|---|
| *C12N 7/04* | (2006.01) | |
| *C12N 1/20* | (2006.01) | |
| *C12P 7/52* | (2006.01) | |
| *C12P 39/00* | (2006.01) | |
| *C12P 7/04* | (2006.01) | |

(52) U.S. Cl.
CPC .......... *C12P 7/04* (2013.01); *C12N 1/20* (2013.01); *C12P 7/52* (2013.01); *C12P 39/00* (2013.01)

(58) Field of Classification Search
CPC .... C12P 7/04; C12P 39/00; C12P 7/52; C12N 1/20
See application file for complete search history.

(56) References Cited

U.S. PATENT DOCUMENTS

| | | | | |
|---|---|---|---|---|
| 4,732,855 | A | 3/1988 | Zeikus | |
| 4,851,344 | A | 7/1989 | Simon et al. | |
| 5,753,474 | A | 5/1998 | Ramey | |
| 6,136,577 | A * | 10/2000 | Gaddy | C12P 7/08 435/161 |
| 7,972,824 | B2 * | 7/2011 | Simpson | C12P 7/14 435/155 |
| 8,017,384 | B2 | 9/2011 | Tsai | |
| 8,058,058 | B2 | 11/2011 | Hickey | |
| 8,062,873 | B2 | 11/2011 | Tsai | |
| 8,101,387 | B2 | 1/2012 | Tsai | |
| 8,119,378 | B2 | 2/2012 | Simpson et al. | |
| 8,293,509 | B2 | 10/2012 | Simpson et al. | |
| 8,309,348 | B2 * | 11/2012 | Tsai et al. | 435/297.2 |

(Continued)

FOREIGN PATENT DOCUMENTS

| | | | | |
|---|---|---|---|---|
| WO | WO 2009/103026 | * | 8/2009 | |
| WO | WO 2012/080421 | * | 12/2011 | C12P 7/04 |

OTHER PUBLICATIONS

Tholozan et al. "Clostridium neopropionicum a strict anaerobic bacterium fermenting ethanol to proionate through acrylate pathway" Arch Microbiol (1992) 157: 249-257.*

(Continued)

*Primary Examiner* — Alexander Kim
(74) *Attorney, Agent, or Firm* — McDonnell Boehnen Hulbert & Berghoff LLP

(57) ABSTRACT

This invention provides methods and systems for the production of propanol. Specifically, the methods and systems of the present invention use symbiotic co-cultures for the production of propanol from syngas.

7 Claims, 3 Drawing Sheets

(56) References Cited

U.S. PATENT DOCUMENTS

| | | | |
|---|---|---|---|
| 8,323,950 B2* | 12/2012 | Burk | C12P 19/32 435/130 |
| 8,329,456 B2 | 12/2012 | Tsai | |
| 8,377,665 B2 | 2/2013 | Barker | |
| 2008/0305540 A1 | 12/2008 | Hickey | |
| 2009/0035848 A1 | 2/2009 | Hickey | |
| 2009/0215163 A1 | 8/2009 | Datta | |
| 2010/0105115 A1 | 4/2010 | Simpson et al. | |
| 2010/0120106 A1* | 5/2010 | Kohn et al. | 435/160 |
| 2011/0104770 A1* | 5/2011 | Tobey | C12P 7/04 435/140 |
| 2011/0201068 A1* | 8/2011 | Pharkya | C12P 7/40 435/136 |
| 2011/0223637 A1* | 9/2011 | Burk | C12P 19/32 435/88 |
| 2011/0229947 A1* | 9/2011 | Zahn | C12P 7/065 435/161 |
| 2011/0256597 A1 | 10/2011 | Hickey et al. | |
| 2012/0040427 A1 | 2/2012 | Bell et al. | |

OTHER PUBLICATIONS

White et al. "The role of tungstat and/or molbdate in the formation of aldehudr oxidoreductase in *Clostridium thermoaceticum* and other acetogens; immunological distances of such enzymes" Arch Microbiol 1992 158 81-84.*

Cindy Lee Van Dover (2000), The Ecology of Deep-Sea Hydrothermal Vents, Princeton University Press, United Kingdom, Chichester, West Sussex, p. 115.*

Essay on Archaebacteria (last viewed on May 19, 2016).*

Abdul Malic et al. (2013), Management of Microbial Resources in the Environment, Springer Dordrecht Heidelberg New York London, pp. 456-457.*

Beale et al. First oceanic measurements of ethanol and propanol, Ocean (2010), vol. 37, Issue 24, pp. 1-5.*

Liu et al., Fermentative production of ethanol from syngas using novel moderately alkaliphilic strains of *Alkalibaculum bacchi*., Bioresource Technology (Epub Oct. 2011), vol. 104, pp. 336-341.*

Schink et al., Pathway of propionate formation from ethanol in *Pelobacter propionicus*., Arch Microbiol (1987), vol. 1987, pp. 321-327.*

Laanbroek et al., Alcohol conversion by *Desulfobulbus propionicus* Lindhorst in the presence and absence of sulfate and hydrogen., Archives of Microbiology (1982), vol. 133, Issue 3, pp. 178-184.*

"Structural and functional relationships in Prokaryotes", L. Barton, Springer 2005, p. 558-569.

"Carbon monoxide-dependent energy metabolism in anaerobic bacteria and archaea", E. Oelgeschelager, M. Rother, Arch. Microbiol., 190, p. 257, 2008.

"Life with carbon monoxide", S. Ragsdale, Critical Reviews in Biochem. and Mol. Biology, 39, p. 165, 2004.

"Bioconversion of synthesis gas into liquid or gaseous fuels", K. Klasson, M. Ackerson, E. Clausen, J. Gaddy, Enzyme and Microbial Technology, 14(8), p. 602, 1992.

"Fermentation of Biomass-Generated Producer Gas to Ethanol", R. Datar, R. Shenkman, B. Cateni, R. Huhnke, R. Lewis, Biotechnology and Bioengineering, 86 (5), p. 587, 2004.

"Microbiology of synthesis gas fermentation for biofuel production", A. Hemstra, J. Sipma, A. Rinzema, A. Stams, Current Opinion in Biotechnology, 18, p. 200, 2007.

"Old Acetogens, New Light", H. Drake, A. Göβner, S. Daniel, Ann. N.Y. Acad. Sci. 1125: 100-128, 2008.

"Reactor design issues for synthesis-gas fermentations" M. Bredwell, P. Srivastava, R. Worden, Biotechnology Progress 15, 834-844, 1999.

"Biological conversion of synthesis gas into fuels", K. Klasson, C. Ackerson, E. Clausen, J. Gaddy, International Journal of Hydrogen Energy 17, p. 281, 1992.

"The Biological Production of Ethanol from Synthesis Gas", J. Vega, S. Prieto, B. Elmore, E. Clausen, J. Gaddy, Applied Biochemistry and Biotechnology, 20-1, p. 781, 1989.

"Clostridium autoethanogenum, Sp-Nov, an Anaerobic Bacterium That Produces Ethanol from Carbon-Monoxide", J. Abrini, H. Naveau, E. Nyns, Archives of Microbiology, 161(4), p. 345, 1994.

"Pathway of propionate formation from ethanol in *Pelobacter propionicus*", Schink, B., Kremer, D. and Hansen, T., Arch. Microbiol. 147, 321-327, 1987.

"Energetics and kinetics of lactate fermentation to acetate and propionate via methylmalonyl-CoA or acrylyl-CoA", S. Seeliger, P. Janssen, B. Schink, FEMS Microbiology Letters, 211, pp. 65-70, 2002.

"Clostridium neopropionicum sp. Nov., a strict anaerobic bacterium fermenting ethanol to propionate through acrylate pathway", J. Tholozan, J. Touzel, E. Samain, J. Grivet, G. Prensier and G. Albagnac, Arch. Microbiol., 157, p. 249-257, 1992.

Balch and Wolfe, 1976, Appl. Environ. Microbiol. 32:781-791.

Balch et al., 1979, Microbiol. Rev. 43:260-296.

"Effect of CO partial pressure on cell-recycled continuous CO fermentation by *Eubacterium limosum* KIST612", I. Chang, B. Kim, R. Lovitt, J. Bang, Process Biochemistry, 37(4), p. 411, 2001.

"*Peptostreptococcus productus* Strain That Grows Rapidly with CO as the Energy-Source", W. Lorowitz, M. Bryant, Applied and Environmental Microbiology, 47(5), p. 961, 1984.

"*Clostridium carboxidivorans* sp. nov., a solvent-producing clostridium isolated from an agricultural settling lagoon, and reclassification of the acetogen *Clostridium scatologenes* strain SL1 as *Clostridium drakei* sp. nov.", J. Liou, D. Ballwin, G. Drake, R. Tanner,International Journal of Systematic and Evolutionary Microbiology, 55(5), p. 2085, 2005.

Playne M., "Propionic and butyric acids", In: Moo-Young M, editor. Comprehensive biotechnology, New York: Pergamon Press, vol. 3, p. 731-759, 1985.

"Influence of environmental parameters on propionic acid upstream bioprocessing by *Propionibacterium acidipropionici*", Seshadri N, Mukhopadhyay S., J. Biotechnology 29, p. 321-328, 1993.

Stackebrandt, E., Cummins, C., Johnson, J., "The Genus Propionibacterium", in The Prokaryotes, E. Balows, H. Truper, M. Dworkin, W. Harder, K. Scheifer, eds., pp. 400-418, 2006.

Wood HG., "Metabolic cycles in the fermentation of propionic acid", in Current Topics in Cellular regulation, Estabrook and Srera RW, eds., New York: Academic Press. vol. 18, p. 225-287, 1981.

"Characterization of the anaerobic propionate-degrading syntrophs *Smithella propionica* gen. nov., sp. nov. and *Syntrophobacter wolinii*", Liu, et al., International journal of Systematic Bacteriology, 49, p. 545-556, 1999.

"Propionic acid fermentation from glycerol: comparison with conventional substrates", Barbirato, F., Chedaille, D. and Bodes, A., Appl Microbiol Biotechnol, 47, p. 441-446, 1997.

"Propionic acid fermentation of glycerol and glucose by *Propionibacterium acidipropionici* and *Propionibacterium freudenreichiissp.* Shermanii", Himmi, E. H., Bodes, A., Boussaid, A. and Hassani, L., Appl Microbiol Biotechnol, 53, p. 435-440, 2000.

"Factors Influencing Rumen Fermentation: Effect of Hydrogen on formation of Propionate", M. Schulman and D. Valentino,Journal of Dairy Science, vol. 59 (8), p. 1444-1451, 1976.

"Regulation of carbon and electron flow in *Propionispira arboris*: Physiological function of hydrogenase and its role in homopropionate formation", Thompson T.E, Conrad R, Zeikus J.G., FEMS Microbiol Lett 22, p. 265-271, 1984.

Interactions between pyruvate and lactate metabolism in *Propionibacterium freudenreichii* subsp. shermanii: In vivo 13C nuclear magnetic resonance studies, Deborde C., Boyaval R 2000, Appl Environ Microbiol 66: 2012-2020.

"Effect of carbon dioxide on propionic acid productivity from glycerol by *Propionibacterium acidipropionici*", An Zhang and Shang-Tian Yang, SIM annual meeting and Exhibition, San Diego, 2008.

"Production of propionic acid", P. Boyaval, C. Corre, Lait, 75, 453-461, 1995.

(56) References Cited

OTHER PUBLICATIONS

G. Gottschalk, "Bacterial Metabolism", 2nd ed., Springer, New York, pp. 242-245, 1986.

Identifying the missings steps of the autotrophic 3-hydroxypropionate CO2 fixation cycle in *Chloroflexus aurantiacus*, PNAS, J. Zarzycki, 106(50), p. 21317, 2009.

A 3-hydroxypropionate/ 4-hydroxybutyrate autotrophic carbon dioxide assimilation pathway in archaea, I. Berg, Science, 318, p. 1782, 2007.

"Plasmid Copy Number Control: Isolation and Characterization of High-Copy-Number Mutants of Plasmid pE194", Weisblum, et al., Journal of Bacteriology, 137:635-643, 1979.

"Conjugative plasmid transfer from *Escherichia coli* to *Clostridium acetobutylicum*", Williams, et al., Journal of General Microbiology, 136:819-826, 1990.

"Genetic Methods in Clostridia", Young, et al., Methods in Microbiology, 29:191-207, 1999.

"Co Dehydrogenase", Ferry, J., Annual Review of Microbiology, 49:305-333, 1995.

\* cited by examiner

METHOD FOR PRODUCTION OF N-PROPANOL AND OTHER C3-CONTAINING PRODUCTS FROM SYNGAS BY SYMBIOTIC CO-CULTURES OF ANAEROBIC MICROORGANISMS

FIELD OF THE INVENTION

The invention provides methods and systems for production of n-propanol and other C3-containing products from syngas using symbiotic co-cultures of anaerobic microorganisms.

BACKGROUND OF THE INVENTION

Propanol is a solvent used industrially, but more importantly, it can be readily dehydrated to produce propylene which is the second largest chemical commodity in the world with production of >70 million tons/per year. Currently propylene is produced mainly by steam-cracking of naphtha or liquid petroleum gas or fluid catalytic cracking of gasoils in very large installations as a secondary product. The steam-cracking a process that makes mainly ethylene and many other co-products, such as butylenes, butadiene and pyrolysis gasoline, all of which need to be purified and to be utilized simultaneously. Other ways to make propylene is in a refinery FCC (fluid catalytic cracking) where propylene is a byproduct from heavy gasoil cracking in proportions between 3 and 15 wt %. Propylene can also be produced by catalytic dehydrogenation of propane. Still another way to make propylene is via metathesis of butenes with ethylene.

Since for many centuries, simple sugars are being fermented into ethanol with the help of *saccharomyces cerevisae*. The last decade's new routes starting from cellulose and hemicelluloses have been developed to ferment more complex carbohydrates into ethanol. Hereto, the carbohydrates need to be unlocked from the lignocellulosic biomass. Biomass consists approximately of 30% cellulose, 35% hemicelluloses and 25% lignin. The lignin fraction cannot be valorised as ethanol because of its aromatic nature, and can only be used as an energy source which is present in many cases in excess for running an industrial plant.

Several microorganisms are able to use one-carbon compounds as a carbon source and some even as an energy source. Carbon dioxide is an important carbon source for phototrophs, sulfate reducers, methanogens, acetogens and chemolithotrophic microorganisms. There are essentially four systems to fix $CO_2$: (1) the Calvin cycle [$CO_2$ fixing enzyme: ribulose-1,5-bisphosphate carboxylase], (2) the reductive citric acid cycle [$CO_2$ fixing enzymes: 2-oxoglutarate synthase, isocitrate dehydrogenase, pyruvate synthase], (3) the acetyl-CoA pathway [$CO_2$ fixing enzyme: acetyl-CoA synthase, linked to CO-dehydrogenase] and (4) the 3-hydroxypropionate cycle [$CO_2$ fixing enzyme: acetyl-CoA carboxylase, propionyl-CoA carboxylase] ("Structural and functional relationships in Prokaryotes", L. Barton, Springer 2005; "Carbon monoxide-dependent energy metabolism in anaerobic bacteria and archaea", E. Oelgeschelager, M. Rother, Arch. Microbiol., 190, p. 257, 2008; "Life with carbon monoxide", S. Ragsdale, Critical Reviews in Biochem. and Mol. Biology, 39, p. 165, 2004).

More recently, more efficient routes that produce synthesis gas from carbon-containing materials and that subsequently is fermented into ethanol are being developed ("Bioconversion of synthesis gas into liquid or gaseous fuels", K. Klasson, M. Ackerson, E. Clausen, J. Gaddy, Enzyme and Microbial Technology, 14(8), p. 602, 1992; "Fermentation of Biomass-Generated Producer Gas to Ethanol", R. Datar, R. Shenkman, B. Cateni, R. Huhnke, R. Lewis, Biotechnology and Bioengineering, 86 (5), p. 587, 2004; "Microbiology of synthesis gas fermentation for biofuel production", A. Hemstra, J. Sipma, A. Rinzema, A. Stams, Current Opinion in Biotechnology, 18, p. 200, 2007; "Old Acetogens, New Light", H. Drake, A. Göβner, S. Daniel, Ann. N.Y. Acad. Sci. 1125: 100-128, 2008).

Synthesis gas can be produced by gasification of the whole biomass without need to unlock certain fractions. Synthesis gas can also be produced from other feedstock via gasification: (i) coal, (ii) municipal waste (iii) plastic waste, (iv) petcoke and (v) liquid residues from refineries or from the paper industry (black liquor). Synthesis gas can also be produced from natural gas via steam reforming or autothermal reforming (partial oxidation).

The biochemical pathway of synthesis gas conversion is described by the Wood-Ljungdahl Pathway. Fermentation of syngas offers several advantages such as high specificity of biocatalysts, lower energy costs (because of low pressure and low temperature bioconversion conditions), greater resistance to biocatalyst poisoning and nearly no constraint for a preset $H_2$ to CO ratio ("Reactor design issues for synthesis-gas fermentations" M. Bredwell, P. Srivastava, R. Worden, Biotechnology Progress 15, 834-844, 1999; "Biological conversion of synthesis gas into fuels", K. Klasson, C. Ackerson, E. Clausen, J. Gaddy, International Journal of Hydrogen Energy 17, p. 281, 1992). Acetogens are a group of anaerobic bacteria able to convert syngas components, like CO, $CO_2$ and $H_2$ to acetate via the reductive acetyl-CoA or the Wood-Ljungdahl pathway.

Several anaerobic bacteria have been isolated that have the ability to ferment syngas to ethanol, acetic acid and other useful end products. *Clostridium ljungdahlii* and *Clostridium autoethanogenum*, were two of the first known organisms to convert CO, $CO_2$ and $H_2$ to ethanol and acetic acid. Commonly known as homoacetogens, these microorganisms have the ability to reduce $CO_2$ to acetate in order to produce required energy and to produce cell mass. The overall stoichiometry for the synthesis of ethanol using three different combinations of syngas components is as follows (J. Vega, S. Prieto, B. Elmore, E. Clausen, J. Gaddy, "The Biological Production of Ethanol from Synthesis Gas", Applied Biochemistry and Biotechnology, 20-1, p. 781, 1989):

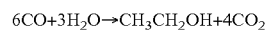

$$6CO + 3H_2O \rightarrow CH_3CH_2OH + 4CO_2$$

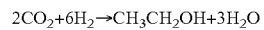

$$2CO_2 + 6H_2 \rightarrow CH_3CH_2OH + 3H_2O$$

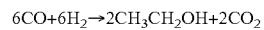

$$6CO + 6H_2 \rightarrow 2CH_3CH_2OH + 2CO_2$$

The primary product produced by the fermentation of CO and/or $H_2$ and $CO_2$ by homoacetogens is ethanol principally according to the first two of the previously given reactions. Homoacetogens may also produce acetate. Acetate production occurs via the following reactions:

$$4CO + 2H_2O \rightarrow CH_3COOH + 2CO_2$$

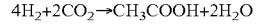

$$4H_2 + 2CO_2 \rightarrow CH_3COOH + 2H_2O$$

*Clostridium ljungdahlii*, one of the first autotrophic microorganisms known to ferment synthesis gas to ethanol was isolated in 1987, as an homoacetogen it favors the production of acetate during its active growth phase (acetogenesis) while ethanol is produced primarily as a non-growth-related product (solventogenesis) ("Biological conversion of synthesis gas into fuels", K. Klasson, C.

Ackerson, E. Clausen, J. Gaddy, International Journal of Hydrogen Energy 17, p. 281, 1992).

*Clostridium autoethanogenum* is a strictly anaerobic, gram-positive, spore-forming, rod-like, motile bacterium which metabolizes CO to form ethanol, acetate and $CO_2$ as end products, beside it ability to use $CO_2$ and $H_2$, pyruvate, xylose, arabinose, fructose, rhamnose and L-glutamate as substrates (J. Abrini, H. Naveau, E. Nyns, "*Clostridium autoethanogenum*, Sp-Nov, an Anaerobic Bacterium That Produces Ethanol from Carbon-Monoxide", Archives of Microbiology, 161(4), p. 345, 1994).

Anaerobic acetogenic microorganisms offer a viable route to convert waste gases, such as syngas, to useful products, such as ethanol, via a fermentation process. Such bacteria catalyze the conversion of $H_2$ and $CO_2$ and/or CO to acids and/or alcohols with higher specificity, higher yields and lower energy costs than can be attained by traditional production processes. While many of the anaerobic microorganisms utilized in the fermentation of ethanol also produce a small amount of propanol as a by-product, to date, no single anaerobic microorganism has been described that can utilize the fermentation process to produce high yields of propanol.

Therefore a need in the art remains for methods using microorganisms in the production of propanol using fermentation with a substrate of $H_2$ and $CO_2$ and/or CO.

SUMMARY OF THE INVENTION

In broadest terms there has been discovered a method for producing propanol and/or propionic acid comprising exposing gaseous substrates selected from the group consisting of carbon monoxide, carbon dioxide and hydrogen or combinations thereof to a symbiotic co-culture comprising a C1-fixing microorganism and a C3-producing microorganism under conditions effective for the symbiotic co-culture to convert the gaseous substrate into propanol or/and into propionic acid. In most cases the gaseous substrate is syngas and the C3-producing microorganism is a propionogen.

In more limited form there has been discovered an anaerobic symbiotic system for conversion of syngas to propanol or/and to propionic acid, the system comprising syngas, culture media, a C1-fixing microorganism and a C3-producing microorganism. Usually, in this form of the invention the C3-producing microorganism is again a propionogen.

BRIEF DESCRIPTION OF THE DRAWINGS

These and other objects, features, and embodiments of the invention will be better understood from the following detailed description taken in conjunction with the drawings, wherein.

DETAILED DESCRIPTION OF THE INVENTION

The invention provides methods for the production of propanol and other C3-containing products from syngas by symbiotic co-cultures of anaerobic microorganisms. In other aspects, the invention provides anaerobic systems for conversion of syngas to propanol.

As used herein, synthesis gas (syngas) is a gas containing carbon monoxide, carbon dioxide and frequently hydrogen. "Syngas" includes streams that contain carbon dioxide in combination with hydrogen and that may include little or no carbon monoxide. "Syngas" may also include carbon monoxide gas streams that may have little or no hydrogen.

As used herein, the term "symbiotic" refers to the association of two or more different types (e.g. organisms, populations, strains, species, genera, families, etc.) of anaerobic microorganisms which are capable of forming a tightly associated metabolic symbiosis. As used herein, the term "co-culture" of microorganisms refers to joint incubation or incubation together, of the symbiotic microorganisms. In the context of the present invention, the co-culture does not require cellular population growth during the joint incubation of the symbiotic microorganisms.

Figure 1:
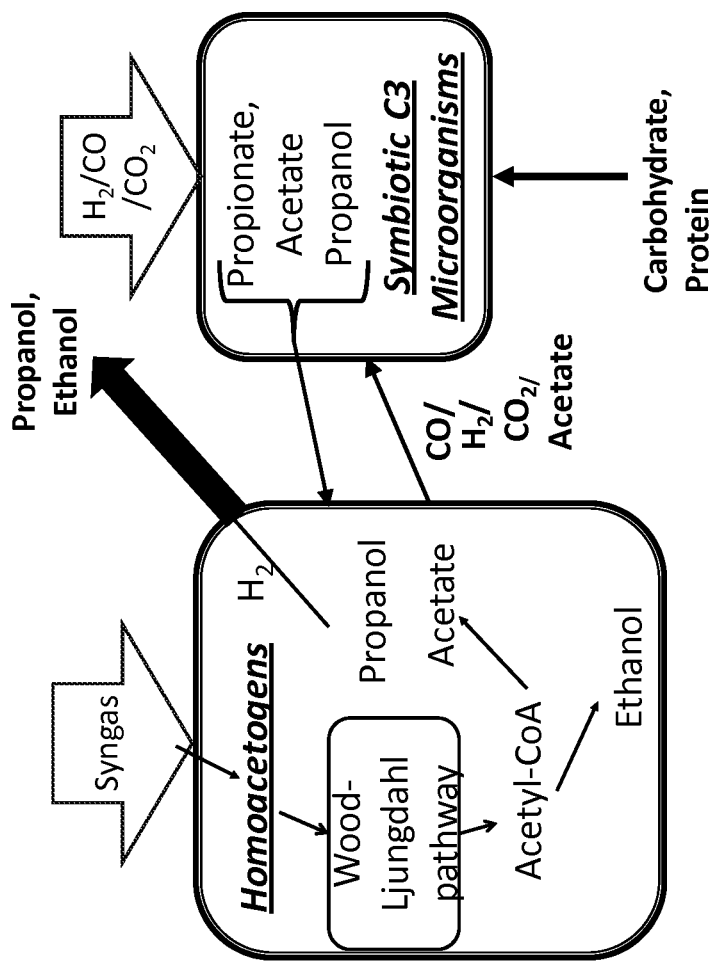
FIG. 1 is a schematic diagram of an embodiment of the symbiotic association of anaerobic microorganism cultures of the invention. The C1-fixing microorganism produces ethanol and acetate from syngas. The symbiotic C3-producing microorganism converts the ethanol, acetate and (secondarily) $H_2/CO/CO_2$ to C3-containing products, namely propionate and propanol. The C1-fixing microorganism also converts the propionate to propanol, which becomes the primary end product.

In an embodiment of the invention illustrated in FIG. 1, two types of anaerobic microorganism are utilized to create the symbiotic co-culture for production of propanol. The first type of microorganism in the symbiotic co-culture is a primary C1-fixing microorganism, which utilizes syngas as the sole carbon and electron source and produces ethanol and acetate as the dissimilatory metabolite products. The second type of microorganism in the symbiotic co-culture is capable of growing on the dissimilatory metabolites of the C1-fixing microorganism (ethanol and acetate) as its sole carbon and/or electron source to produce a C3-carbon molecule, such as propanol or propionic acid, as its primary product or together with syngas (as additional carbon and/or electron source) convert the metabolites of the C1-carbon fixing microorganism to C3-carbon molecules. This second microorganism shall be referred to herein as the C3-producing microorganism. Advantageously, the C1-fixing microorganism may also be capable of converting the propionate produced by the C3-producing microorganism into propanol.

The C1-fixing microorganisms of the invention are also homoacetogens. Homoacetogens have the ability, under anaerobic conditions, to produce acetic acid and ethanol from the substrates, $CO+H_2O$, or $H_2+CO_2$ or $CO+H_2+CO_2$. The CO or $CO_2$ provide the carbon source and the $H_2$ or CO provide the electron source for the reactions producing acetic acid and ethanol. The primary product produced by the fermentation of CO and/or $H_2$ and $CO_2$ by homoacetogens is ethanol principally according to the two previously given reactions so that the C1 fixing microorganisms are acting as solventogenic homoacetogens using the acetyl-CoA pathway.

C1-fixing microorganisms suitable for use in the inventive method include, without limitation, homoacetogens such as *Clostridium ljungdahlii, Clostridium autoethanogenum, Clostridium ragsdalei,* and *Clostridium coskatii.* Additional C1 fixing microorganisms that are suitable for the invention include *Alkalibaculum bacchi, Clostridium thermoaceticum,* and *Clostridium aceticum.*

Figure 2:
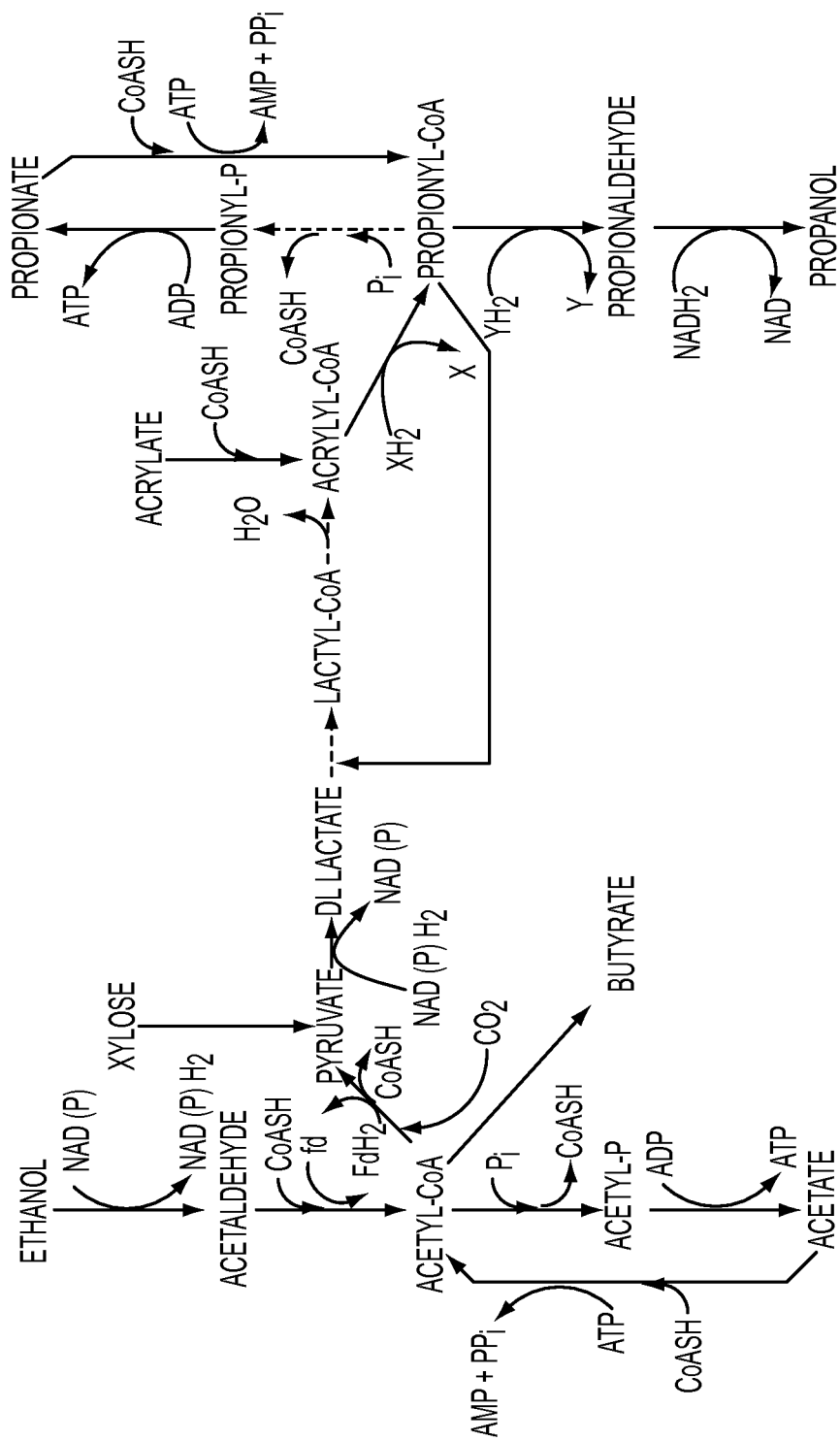
FIG. 2 is a detailed illustration of the methylmalonyl-succinate pathway used by anaerobic microorganisms for C3 (propionate) production.
Figure 3:
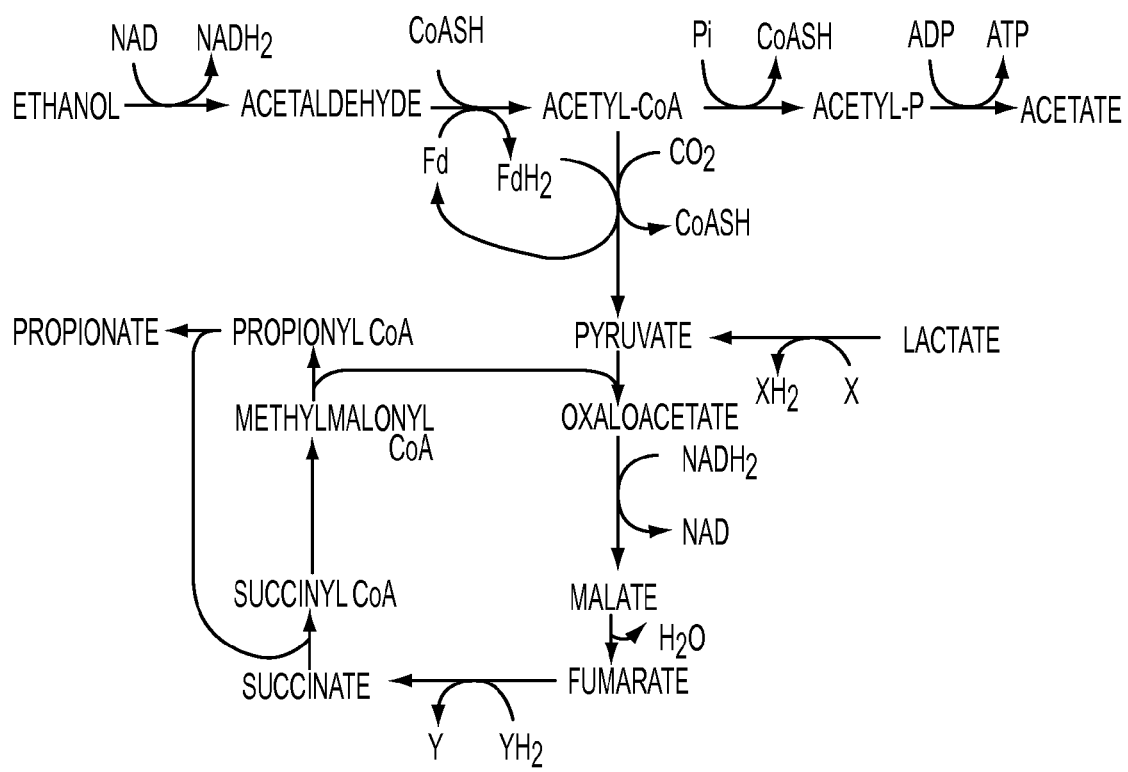
FIG. 3 is a detailed illustration of the lactate-acrylate pathway used by anaerobic microorganisms for C3 (propionate/propanol) production.

In this invention the symbiotic C3-producing microorganisms are capable of growing on ethanol and/or acetate as their primary carbon source. These microorganisms include, but are not limited to the organisms and their pathways described above and include: *Pelobacter propionicus, Clostridium neopropionicum, Clostridium propionicum, Desulfobulbus propionicus, Syntrophobacter wolinii, Syntrophobacter pfennigii, Syntrophobacter fumaroxidans, Syntrophobacter sulfatireducens, Smithella propionica, Desulfotomaculum thermobenzoicum* subspecies *thermosymbioticum, Pelotomaculum thermopropionicum,* and *Pelotomaculum schinkii.* In particular embodiments of the invention, the C3-producing microorganisms are propionogens. Propionogens refers to any microorganism capable of converting syngas intermediates, such as ethanol and acetate, to propionic acid and propanol. Propionogens of the invention utilize one of at least two distinct pathways for the conversion of acetate and ethanol to propionate—the methylmalonyl-succinate pathway (shown in FIG. 2) and the lactate-acrylate pathway (shown in FIG. 3).

*Pelobacter propionicus*, using the dicarboxylic acid pathway, has been shown to grow on ethanol as substrate while producing propionate in presence of $CO_2$ (Schink, B., Kremer, D. and Hansen, T., "Pathway of propionate formation from ethanol in *Pelobacter propionicus*", Arch. Microbiol. 147, 321-327, 1987 and S. Seeliger, P. Janssen, B. Schink, "Energetics and kinetics of lactate fermentation to acetate and propionate via methylmalonyl-CoA or acrylyl-CoA", FEMS Microbiology Letters, 211, pp. 65-70, 2002). When ethanol is fed together with CO2 and hydrogen, significant amounts of propanol are produced. Ethanol is converted into acetyl-CoA (via acetaldehyde) while producing electrons for the carboxylation of acetyl-CoA into pyruvate, catalysed by pyruvate synthase. Combined with the dicarboxylic acid pathway propionate is produced from ethanol and CO2 (Schink et al., 1987).

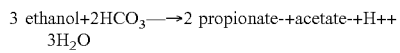

3 ethanol+2HCO$_3$⁻→2 propionate-+acetate-+H++ 3H$_2$O

*Pelobacter propionicus* is not able to reductively convert acetate and $CO_2$ into propionate whereas *Desulfobulbus propionicus* does make propionate from acetate and $CO_2$ (Schink et al., 1987).

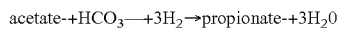

acetate-+HCO$_3$⁻+3H$_2$→propionate-+3H$_2$0

*Clostridium neopropionicum* (strain X4), using the acrylate pathway, is able to convert ethanol and $CO_2$ into acetate, propionate and some propanol (J. Tholozan, J. Touzel, E. Samain, J. Grivet, G. Prensier and G. Albagnac, "*Clostridium neopropionicum* sp. Nov., a strict anaerobic bacterium fermenting ethanol to propionate through acrylate pathway", Arch. Microbiol., 157, p. 249-257, 1992). As for the dicarboxylic acid pathway, the intermediate acetyl-CoA produced from the substrate ethanol is linked to the acrylate pathway via the pyruvate synthase that converts acetyl-CoA into pyruvate by carboxylation with $CO_2$.

Thus, when the symbiotic cultures of the present invention have the capability in a spatially separated symbiotic relationship or as co-cultures to produce n-propanol from gaseous carbon and electron sources. Suitable sources of carbon and electron sources for the cultures include "waste" gases such as syngas, oil refinery waste gases, steel manufacturing waste gases, gases produced by steam, autothermal or combined reforming of natural gas or naphtha, biogas and products of biomass, coal or refinery residues gasification or mixtures of the latter. Sources also include gases (containing some $H_2$) which are produced by yeast, clostridial fermentations, and gasified cellulosic materials. Such gaseous substrates may be produced as byproducts of other processes or may be produced specifically for use in the methods of the present invention. Those of skill in the art will recognize that any source of substrate gas may be used in the practice of the present invention, so long as it is possible to provide the microorganisms of the co-culture with sufficient quantities of the substrate gases under conditions suitable for the bacterium to carry out the fermentation reactions.

In one preferred embodiment of the invention, the source of CO, $CO_2$ and $H_2$ is syngas. Syngas for use as a substrate may be obtained, for example, as a gaseous product of coal or refinery residue gasification. Syngas may also be produced by reforming natural gas or naphtha, for example by the reforming of natural gas in a steam methane reformer. Alternatively, syngas can be produced by gasification of readily available low-cost agricultural raw materials expressly for the purpose of bacterial fermentation, thereby providing a route for indirect fermentation of biomass to alcohol. There are numerous examples of raw materials which can be converted to syngas, as most types of vegetation could be used for this purpose. Suitable raw materials include, but are not limited to, perennial grasses such as switchgrass, crop residues such as corn stover, processing wastes such as sawdust, byproducts from sugar cane harvesting (bagasse) or palm oil production, etc. Those of skill in the art are familiar with the generation of syngas from such starting materials. In general, syngas is generated in a gasifier from dried biomass primarily by pyrolysis, partial oxidation, and steam reforming, the primary products being CO, $H_2$ and $CO_2$. The terms "gasification" and "pyrolysis" refer to similar processes; both processes limit the amount of oxygen to which the biomass is exposed. The term "gasification" is sometimes used to include both gasification and pyrolysis.

Combinations of sources for substrate gases fed into the fermentation process may also be utilized to alter the concentration of components in the feed stream to the bioreactor. For example, the primary source of CO, $CO_2$ and $H_2$ may be syngas, which typically exhibits a concentration ratio of 37% CO, 35% $H_2$, and 18% $CO_2$, but the syngas may be supplemented with gas from other sources to enrich the level of CO (i.e., steel mill waste gas is enriched in CO) or $H_2$.

The symbiotic co-cultures of the present invention must be cultured under anaerobic conditions. As used herein, "anaerobic conditions" means the level of oxygen ($O_2$) is below 0.5 parts per million in the gas phase of the environment to which the microorganisms are exposed. One of skill in the art will be familiar with the standard anaerobic techniques for culturing these microorganisms (Balch and Wolfe, 1976, Appl. Environ. Microbiol. 32:781-791; Balch et al., 1979, Microbiol. Rev. 43:260-296). These culturing techniques entail the aid of an anaerobic chamber for preparing culture materials and a gas exchange manifold to establish the desired gas phase for culture in sealed tubes or vessels.

Currently, no natural symbiotic pairings able to produce propanol or acid propionic from syngas have been found in natural environments. However, microorganisms from natural environments, when paired together under the correct nutrient conditions and selection pressures can be forced to form these "unnatural" metabolic symbiotic pairings which will produce propanol from syngas.

Symbiotic cultures for use in the invention can be generated in several ways. One approach involves using nutrient selection pressures to form a metabolic symbiosis between at least two of the microorganisms found in an environmental sample containing a mixed anaerobic microbial community. In this method, the only carbon and electron sources available for microbial growth are either syngas and/or syngas fermentation products, such as ethanol and acetate.

Under these nutrient selection pressures, microorganisms capable of growing on these nutrients will be enriched.

A variation of the process for forming symbiotic associations described above involves dilution. This process allows the very slow growing C3-producing propionogens in the sample to reach a higher cell density. Dilution of enrichment cultures can proceed with either a continuously fed anaerobic fermenter or manually through serial dilutions of enrichment samples. Both dilution techniques apply the same nutrient selection pressure of carbon and electron sources described previously.

Another method for establishing a symbiotic association capable of converting syngas to propanol involves the growing of two or more defined cultures and establishing the pairing of these separate cultures. A person skilled in the art would appreciate that there are numerous methods of pairing two or more defined cultures. For example, one method involves first growing a known C1-fixing homoacetogen in a fermenter with syngas as the only carbon and electron source. In a preferred embodiment, the homoacetogen will produce ethanol and, at the same time, a known C3-producing propionogen culture is grown in a separate fermentor. Once the homoacetogen has reached steady state with respect to ethanol and/or acetate productivity, a known C3-producing propionogen culture is seeded into the fermenter.

Another method of pairing involves first growing the C3-producing propionogen in a fermenter until maximum productivity target of propionic acid+propanol has been reached. This stage of fermentation should have syngas as the sparging gas to acclimate the culture to syngas and to provide $CO_2$ for propionic acid production. Once the maximum productivity target has been reached a seed culture of the C1-fixing homoacetogen is added directly to the fermenter containing the C3-producing culture. Syngas mass transfer to the fermentation vessels are gradually increased to balance the gas consumption of the C1-fixing homoacetogen. The ethanol or acetate used to grow the C3-producing propionogen is gradually decreased to zero as the C1-fixing homoacetogen begins to provide this substrate. A modification of this last method of establishing a symbiotic culture involves first growing the C3-producing propionogen culture in a fermenter with a biofilm support material that is either stationary or floating within the reactor. US Patent Publication 20090035848, which is herein incorporated in its entirety, shows the use of floating support material in a moving bed bioreactor. An example of such material is the Mutag Biochips. This method allows the C3-producing microorganism to first establish a biofilm on the carrier material thereby increasing the cell retention time versus the hydraulic retention of the fermenter. Again, target propionic acid productivity is reached before seeding the fermenter with the C1-fixing homoacetogen.

The last method to establish a symbiotic culture capable of producing propanol from syngas involves the initial mixing together of two or more cultures, one of which is a C1-fixing homoacetogen capable of growing on syngas and producing ethanol and acetate. The other culture(s) is a C3-producing propionogen capable of converting ethanol or acetate to propionic acid. Ethanol and acetate feed can gradually be decreased to zero as the production of these substrates by the C1-fixing homoacetogens increases to balance the substrate consumption.

A suitable medium composition used to grow and maintain symbiotic co-cultures or separately grown cultures used for sequential fermentations, includes a defined media formulation. The standard growth medium is made from stock solutions which result in the following final composition per Liter of medium. The amounts given are in grams unless stated otherwise. Minerals: NaCl, 2; $NH_4Cl$, 25; KCl, 2.5; $KH_2PO_4$, 2.5; $MgSO_4.7H_2O$, 0.5; $CaCl_2.2H_2O$, 0.1. Trace metals: $MnSO_4.H_2O$, 0.01; $Fe(NH_4)_2(SO_4)_2.6H2O$, 0.008; $CoCl_2.6H2O$, 0.002; $ZnSO_4.7H2O$, 0.01; $NiCl_2.6H2O$, 0.002; $Na_2MoO_4.2H_2O$, 0.0002, $Na_2SeO_4$, 0.001, $Na_2WO_4$, 0.002. Vitamins (amount, mg): Pyridoxine HCl, 0.10; thiamine HCl, 0.05, riboflavin, 0.05; calcium pantothenate, 0.05; thioctic acid, 0.05; p-aminobenzoic acid, 0.05; nicotinic acid, 0.05; vitamin B12, 0.05; mercaptoethanesulfonic acid, 0.05; biotin, 0.02; folic acid, 0.02. A reducing agent mixture is added to the medium at a final concentration (g/L) of cysteine (free base), 0.1; $Na_2S.2H_2O$, 0.1. Medium compositions can also be provided by yeast extract or corn steep liquor or supplemented with such liquids.

The methods of the present invention can be performed in any of several types of fermentation apparatuses that are known to those of skill in the art, with or without additional modifications, or in other styles of fermentation equipment that are currently under development. Examples include but are not limited to bubble column reactors, two stage bioreactors, trickle bed reactors, membrane reactors, packed bed reactors containing immobilized cells, etc. These apparatuses will be used to develop and maintain the C1-fixing homoacetogen and C3-producing propionogen cultures used to establish the symbiotic metabolic association. The chief requirements of such an apparatus include:

a. Axenicity;
b. Anaerobic conditions;
c. Suitable conditions for maintenance of temperature, pressure, and pH;
d. Sufficient quantities of substrates are supplied to the culture;
e. Optimum mass transfer performance to supply the gases to the fermentation medium
e. The end products of the fermentation can be readily recovered from the bacterial broth.

The fermentation reactor may be, for example, a traditional stirred tank reactor, a column fermenter with immobilized or suspended cells, a continuous flow type reactor, a high pressure reactor, a suspended cell reactor with cell recycle, and other examples previously listed. Furthermore, reactors may be arranged in a series and/or parallel reactor system which contains any of the above-mentioned reactors. For example, multiple reactors can be useful for growing cells under one set of conditions and generating n-propanol (or other products) with minimal growth under another set of conditions.

In general, fermentation of the symbiotic co-culture will be allowed to proceed until a desired level of propanol is produced in the culture media. Preferably, the level of propanol produced is in the range of 2 grams/liters to 75 grams/liters and most preferably in the range of 4 grams/liter to 50 grams/liter. Alternatively, production may be halted when a certain rate of production is achieved, e.g. when the rate of production of a desired product has declined due to, for example, build-up of bacterial waste products, reduction in substrate availability, feedback inhibition by products, reduction in the number of viable bacteria, or for any of several other reasons known to those of skill in the art. In addition, continuous culture techniques exist which allow the continual replenishment of fresh culture medium with concurrent removal of used medium, including any liquid products therein (i.e. the chemostat mode). Also techniques of cell recycle may be employed to control the cell density and hence the volumetric productivity of the fermentor.

The products that are produced by the microorganisms of this invention can be removed from the culture and purified by any of several methods that are known to those of skill in the art. For example, propanol can be removed by distillation at atmospheric pressure or under vacuum, by adsorption or by other membrane based separations processes such as pervaporation, vapor permeation and the like and further processed such as by chemical/catalytic dehydration to produce propylene.

This invention is more particularly described below and the Examples set forth herein are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The terms used in the specification generally have their ordinary meanings in the art, within the context of the invention, and in the specific context where each term is used. Some terms have been more specifically defined to provide additional guidance to the practitioner regarding the description of the invention.

EXAMPLES

The Examples which follow are illustrative of specific embodiments of the invention, and various uses thereof. They are set forth for explanatory purposes only, and are not to be taken as limiting the invention.

Example 1

C13-Labeled Propionic Acid Conversion to Propanol

To demonstrate that homoacetogen cultures growing on syngas convert propionic acid to propanol and other fermentation byproducts, C13-propionic acid experiments were performed. C13-propionic acid was fed to homoacetogen culture, *Clostridium coskatii*, at a concentration of 100 mM in a serum bottle and incubated at 37° C. Samples were withdrawn from the serum bottles at 2 hrs, 24 hrs and 1 week. GC-MC was used to identify the products containing the heavy stable isotope C13. C13 products were found in the propanol peak and there was no propanol produced without the C13 label. In addition there were no other products formed that contained the C13 heavy carbon isotope or its mass fragments demonstrating that homoacetogens can reduce propionic acid to propanol and no other end products when growing on syngas.

Example 2

Propionic Acid to Propanol in Homoacetogen Fermenters

An ethanol producing homoacetogen fermenter was continuously fed propionic acid while maintaining the fermentation broth controlled at a pH of 5.0 to investigate the rate and yield of propanol. The initial concentration of ethanol in the fermenter was 500 mmol/L before propionic acid feed was started. Concentrations of propanol reached 167 mmol/L in the fermenter at a feed rate of 200 mmol/L/hr propionic acid. Residual propionic acid in the fermenter was 27 mmol/L; therefore the conversion efficiency to propanol was 97%. The concentration of ethanol in the fermenter steadily decreased as the concentration of propanol increased. At 167 mmol/L propanol the fermenter contained 250 mmol/L of ethanol. This ratio of alcohols demonstrates an electron balance based on the gas consumption rates of syngas in the fermenter. A production rate of propanol at steady state of 0.22 g/L/hr was achieved in the fermenter. The results show both high conversion efficiency and rates of propionic acid to propanol by homoacetogenic microorganisms growing on syngas. In addition, these results also showed no impact on syngas consumption with propanol concentrations as high as 10 g/L (167 mmol/L). These results demonstrate that in a co-fermentation with the homoacetogen partner such as *C. coskatii* propionic acid is readily converted to propanol and the residual acetic acid is recycled and converted to propanol by this symbiotic co culture.

Example 3

Propionic Acid Production from Ethanol in Fermenters

A fermenter was started with *Clostridium neopropionicum* growing on ethanol as the source of electrons and bicarbonate and ethanol as the source of carbon. Ethanol concentration in the media feed was 213 mmol/L. The fermenter reached a concentration of 89 mmol/L propionic acid, 5 mmol/L of propanol, and a residual ethanol of 27 mmol/L at steady state. This represented a conversion efficiency of 76% from ethanol to propionic acid based on a theoretical conversion stoichiometry of 1.5 moles of ethanol per mole of propionic acid produced. Other reaction products included acetic acid and small amounts of butyric acid.

Example 4

Propanol Co-Culture of a Homoacetogen and a Propionogen that Uses the Acrylate Pathway A homoacetogenic bacterial culture of *C. coskatii*, grown on syngas in a fermenter and producing ethanol and acetate was mixed in with an anaerobic batch (bottle) culture of *C. neopropionicum*, which has the lactate acrylate pathway, grown on ethanol and producing propionate and low levels of propanol. The co-cultures, in bottles, were incubated under syngas with pH adjustment by addition of a dilute sodium bicarbonate ($NaHCO_3$) solution. The initial ethanol concentration in the co-cultures was approximately 180 mM (8.3 g/L), which was derived from the syngas fermentation. The initial propionate concentration was ~3 mM (0.22 g/L), which was introduced into the co-culture mixture with the *C. neopropionicum* culture medium. The co-cultures were grown under syngas atmosphere of initial composition of ~38% CO, ~38% $H_2$, ~15% $CO_2$ and ~9% $CH_4$. The pH was adjusted periodically to maintain the level at or above pH 6.0. After 48 hrs samples were taken and analyzed. The analysis showed that ethanol was consumed and propanol production peaked at 36 mM (2.2 g/L), a level 12 times the initial molar propionate concentration, demonstrating that the propanol was derived from the syngas-produced ethanol and was not just the product of conversion of the initial propionate present. The propionate concentration also increased under these conditions to 33 mM (2.4 g/L) at day-three of incubation (when the experiment was terminated). These results indicate that a co-culture of a solventogenic syngas-metabolizing homoacetogen and an ethanol-metabolizing propionate-producing anaerobic bacterium can produce propanol from syngas-derived ethanol at a significant yield.

Example 5

Propanol Production by Co-Culture of a Homoacetogen and a Propionogen that Uses the Methylmalonyl Succinate Pathway A homoacetogenic bacterial culture of *C. coskatii*, grown on syngas in a fermenter and producing ethanol was mixed with an anaerobic, batch (bottle), culture of *Pelobacter propionicus*, which uses the methylmalonate-succinate pathway, grown on ethanol and producing propionate and low levels of propanol. The initial ethanol concentration in the co-culture was approximately 120 mM (5.6 g/L), the majority of which was derived from the syngas fermentation. The initial propionate concentration was ~1.8 mM, which was introduced into the co-culture mixture with the *P. propionicus* culture medium. The co-culture was incubated in a bottle at 30° C. with agitation under a syngas atmosphere with an initial composition of approximately 38% CO, 38% $H_2$, 15% $CO_2$ and 9% $CH_4$. The initial pH of the co-culture mixture was adjusted to ~7.0 by addition of a dilute sodium bicarbonate ($NaHCO_3$) solution. Samples taken for analysis at the end of an 8 day incubation period showed ethanol utilization and propanol production. Approximately 40% of the original ethanol present in the mixture was consumed (47.44 mM) which resulted in a final total C3 compound (propanol+propionate) concentration of 17.5 mM. Propanol represented the majority of the C3 production with a final concentration of 14.43 mM while the propionate concentration was 3.07 mM. These concentrations represent a 13 and 1.67 times increase above initial values for propanol and propionate, respectively and a net production of 14.56 mM C3 compounds. There was no net production of C3 compounds in a control experiment where the *Pelobacter propionicus* cells were not present. These results demonstrate that a co-culture of a solventogenic syngas-metabolizing homoacetogen and an ethanol-metabolizing propionate-producing anaerobic bacterium can produce propanol from syngas-derived ethanol at a significant yield.

The invention claimed is:

1. A method for producing propanol comprising exposing gaseous substrates selected from the group consisting of a carbon source and an electron source to a symbiotic co-culture comprising a naturally occurring C1-fixing microorganism and a naturally occurring C3-producing microorganism under conditions effective for the symbiotic co-culture to convert the gaseous substrate into propanol wherein the propanol produced is ≥2 grams/liter;

wherein the C1-fixing microorganism is selected from the group consisting of *Clostridium Coskatii, Clostridium ljungdahlii, Clostridium authoethanogenum, Clostridium ragsdalei, Alkalibaculum bacchi, Clostridium thermoaceticum,* and *Clostridium aceticum*; and wherein the C3-producing microorganism is selected from the group consisting of *Clostridium neopropionicum, Clostridium propionicum, Pelobacter propionoicus, Desulfobulbus propionicus, Syntrophobacter wolinii, Syntrophobacter pfennigii, Syntrophobacter fumaroxidans, Syntrophobacter sulfatireducens, Smithella propionica, Desulfotomaculum thermobenzoicum* subspecies *thermosyntrophicum, Pelotomaculum thermopropionicum,* and *Pelotomaculum schinkii*; and wherein the carbon source is at least one of carbon monoxide and carbon dioxide and the electron source is at least one of hydrogen and carbon monoxide.

2. The method of claim 1 wherein the C1-fixing microorganism is a solventogenic acetogen, using the acetyl-CoA pathway.

3. The method of claim 1 wherein the C3-producing microorganism is a propionogen.

4. The method of claim 3 wherein the propionogen uses the lactate acrylate pathway for the production of propionate.

5. The method of claim 3 wherein the propionogen uses the methylmalonyl-succinate pathway for the production of propionate.

6. The method of claim 1 wherein the gaseous substrate is syngas.

7. The method of claim 1 wherein the pH of the symbiotic co-culture is maintained between about 5.0 to 7.0.

* * * * *